United States Patent [19]

Tóth et al.

[11] Patent Number: 4,866,062
[45] Date of Patent: Sep. 12, 1989

[54] 1,4-DISUBSTITUTED PIPERAZINES, PHARMACEUTICAL COMPOSITIONS THEREOF AND METHOD OF USE

[75] Inventors: Edit Tóth, Budapest; Béla Kiss, Vecsés; József Türley, Budapest; Éva Pálosi, Budapest; István Hajdu, Budapest; László Szporny, Budapest; Dóra Groó, Budapest; Erzsébet Lapis, Budapest; István Lászlovszky, Budapest, all of Hungary

[73] Assignee: Richter Gedeon Vegyeszeti Gyar, Budapest, Hungary

[21] Appl. No.: 41,234

[22] Filed: Apr. 22, 1987

[30] Foreign Application Priority Data

Apr. 28, 1986 [HU] Hungary ............... 1750/86

[51] Int. Cl.$^4$ .................. A61K 31/495; C07D 295/08
[52] U.S. Cl. ...................................... 514/255; 544/397
[58] Field of Search ......................... 544/397; 514/255

[56] References Cited

U.S. PATENT DOCUMENTS 2,988,551 6/1961 Morren ........................... 544/397
4,202,896 5/1980 Gootjes ........................... 544/397

FOREIGN PATENT DOCUMENTS 530795 11/1954 Belgium ............................. 544/397
530796 11/1954 Belgium ............................. 544/397
530797 11/1954 Belgium ............................. 544/397
99148 1/1984 European Pat. Off. ........... 544/397
396007 1/1966 Switzerland ...................... 544/397

OTHER PUBLICATIONS

Morren, 1,4-Bis(2-Trydroxyethyl)Piperazine Derivatives CA vol. 56, 4778d (1962) e.g. US 2988551.
Hohensee, the Pharmacological Action of Some Basic Esters CA. vol. 50, 4405b (1956).
Riffkin et al., Syntheses of Amino Ethers with Potential Pharmacological Activity, CA. vol. 50, 16792d (1956).
Morren et al., New 1,4–Disubstituted Derivatives of Piperazine and Their Antihistaminic Properties, CA. vol. 53, 2240e (1959).
Morren, Piperazine Derivatives, CA. vol. 53, 17156i (1959) e.g. Bel. 530795-530797.
Carlsson (1988) Perspectives in Psychopharmacology Collection of Papers in Honor of E. Usdin. Alan L. Riss, Inc., pp. 209-233.
Gottries (1985) Psychopharmacology 86:245-252.

Primary Examiner—Cecilia Shen
Attorney, Agent, or Firm—Keil & Weinkauf

[57] ABSTRACT

The invention relates to novel 1,4-disubstituted piperazine derivatives of the general formula (I), pharmaceutically acceptable acid addition salts thereof, pharmaceutical compositions containing them and a process for their preparation.

In the general formula (I)

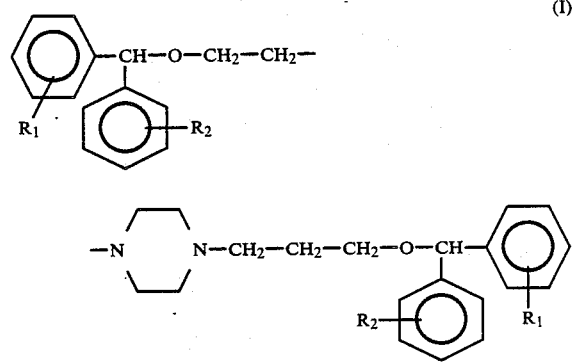

$R_1$ and $R_2$ are the same or different and stand for hydrogen or halogen or a lower alkyl, trihalomethyl or lower alkoxy group.

The compounds of the general formula (I) are therapeutically useful for the treatment of diseases arising from a hypofunction of the dopaminergic system.

5 Claims, No Drawings

1,4-DISUBSTITUTED PIPERAZINES, PHARMACEUTICAL COMPOSITIONS THEREOF AND METHOD OF USE

The invention relates to novel therapeutically useful 1,4-disubstituted piperazine derivatives of the general formula (I),

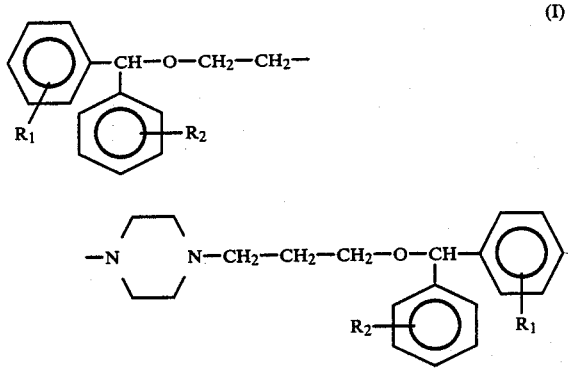

wherein
$R_1$ and $R_2$ are the same or different and stand for hydrogen or halogen or a lower alkyl, trihalomethyl or lower alkoxy group,
as well as their pharmaceutically acceptable acid addition salts and pharmaceutical preparations containing these compounds.

According to an other aspect of the invention, there is provided a process for the preparation of the new compounds of the general formula (I) and acid addition salts thereof.

The compounds of the general formula (I) may contain one or more asymmetric carbon atoms and thus they may exist in various stereoisomeric forms. Therefore, the compounds of the general formula (I) may be bases, acid addition salts, racemates, separated optical isomers and the mixtures thereof as well as the solvates, e.g. hydrates, of these compounds.

Compounds with a similar structure have been described in several papers (CA 45, 577f; 50, 4405b; and 50, 16792c) and patents [Belgian patent specifications Nos. 530,795 and 530,797; as well as U.S. patent specification No. 2,988,551]. These known compounds are symmetrically substituted 1,4-bis[2-(benzhydryloxy)ethyl]piperazine, or 1,4-bis[3-(benzhydryloxy)propyl]-piperazine derivatives, respectively, possessing an antihistamine effect.

Unexpectedly, it has been found that the pharmacological action of the novel compounds of the general formula (I), i.e. the asymmetrically disubstituted piperazine derivatives of the invention, is substantially different from that of the piperazine derivatives known from the literature.

The novel compounds of the general formula (I) and their pharmaceutically acceptable salts show a strong, selective dopaminergic activity on the central nervous system and thus they are useful for treating diseases occurring as a consequence of the degeneration and/or hypofunction of the dopaminergic system, such as depression, parkinsonism, several neuroendrocrine illnesses, "ageing", impotence and the like.

The dopaminergic activity of the compounds of the invention and their salts was determined by in vivo tests carried out on mice and rats.

(a) Measurement of the modification of the locomotor activity

The hypermotility induced by L-DOPA [L-(3,4-dihydroxyphenyl)-α-alanine] is influenced by dopaminergic substances. The method of N. P. Plotnikoff et al. ["The Thyroid Axis, Drugs and Behaviour", Raven Press N. Y., pp. 103–113 (1974)] was used for this study.

Male Hann-Wistar rats weighing 160 to 180 g were used. Animal groups of 5 members were intraperitoneally (i.p.) treated with 40 mg/kg of body-weight (abbreviated; mg/kg) of pargyline [N-methyl-N-(2-propynyl)-benzylamine], and after 60 minutes the compounds to be tested were orally given in a dose of 30 mg/kg as an 0.5% Tween suspension. The control groups were treated with placebo (i.e. with 10 mg/kg of an aqueous solution containing 0.5% of Tween in distilled water). Thirty minutes later, 100 mg/kg of L-DOPA were intraperitoneally administered. The locomotor activity of the animals was registered by using a 5-channel VKI (Type UPAMS-01) motimeter (activity meter) for 3 hours following the treatment. (In the course of the time of the measurement, the time of the active movement of the animals was registered.) The results are given as the percentage of the control in Table 1.

In Table 1, the following abbreviations are used:
n: number of the animals
i.p.: intraperitoneal(ly)
p.o.: oral(ly)
L-DOPA: [L-(3,4-dihydroxyphenyl)-α-alanine]
$\bar{x} \pm SE$:: average±standard error
In Table 1, the following compounds are listed:
A: 1-[2-[bis(4-fluorophenyl)methoxy]ethyl]-4-[3-[bis(4-fluorophenyl)methoxy]propyl]piperazine dimaleate
B: 1-[2-[(4-methoxyphenyl)-(3-trifluoromethylphenyl)-methoxy]ethyl]-4-[3-[(4-methoxyphenyl)-(3-trifluoromethylphenyl)methoxy]propyl]piperazine dimaleate
C: 1-[2-[bis(4-chlorophenyl)methoxy]ethyl]-4-[3-[bis(4-chlorophenyl)methoxy]propyl]piperazine dimaleate
D: 1-[2-[(2-methylphenyl)-(4-fluorophenyl)methoxy]ethyl]-4-[3-[2-methylphenyl)-(4-fluorophenyl)methoxy]propyl]piperazine dimaleate
E: 1-[2-(diphenylmethoxy)ethyl]-4-[3-(diphenylmethoxy)propyl]piperazine dimaleate

TABLE 1

| Compound | Dose mg/kg p.o. | Locomotor activity i.e. total movements/3 hours as percentage of the control | n |
|---|---|---|---|
| A | 30 | 175 ± 9.3 | 15 |
| B | 30 | 151 ± 7.1 | 15 |
| C | 30 | 202 ± 9.8 | 15 |
| D | 30 | 157 ± 8.4 | 15 |
| Control (Placebo) | — | 100 ± 10.4 | 15 |
| Control (Placebo) | $\bar{x} \pm S.E. =$ | 1986 ± 208.5 sec | |

It is obvious from the above results that the compounds of the invention are capable to increase significantly the hyperactivity induced by L-DOPA and thus they provide an important improvement in diseases arising from a dopamine-deficiency (in dopamine-deficient conditions).

(b) Inhibition of the neurotoxic action of 1-methyl-4-phenyl-1,2,3,6-tetrahydropyridine (MPTP)

In 1979 it was reported that MPTP caused the degeneration of the dopaminergic system in men and monkeys [G. C. Davis et al.: Psychiat. Res. 1, 249 (1979); R. S. Burns et al.: Proc. Natl. Acad. Sci. (USA), 80, 4546 (1983)]; the selective dopaminergic system-damaging effect on mice of this compound was also shown [see, e.g. H. Hallman et al.: Eur. J. Pharmacol. 97, 133 (1984); E. Pileblad et al.: Neuropharmacol. 24, 689 (1986)]. The selective dopaminergic system-damaging effect caused by MPTP on test animals can be considered to be a process analogous to the degenerative and hypofunctional diseases of the human dopaminergic system and thus it is a suitable model for investigating compounds useful for the therapeutical treatment of diseases connected with the pathological functioning of the dopaminergic system [A. J. Bradbury et al.: The Lancet 1985, 1444; H. Przuntek et al.: Life sci. 37, 1195 (1985)].

For these investigations, male CFY mice (LATI, Gödöllő, Hungary) weighing 20–25 g were used. The compounds to be tested were homogenized in 1% Tween 80 solution and administered to the animals in a dose of 0.1 mmole/kg (in the route given in the Table) at 1 hour before administering MPTP. MPTP was freshly dissolved in physiological saline solution and subcutaneously given to the mice in a dose of 70 mg/kg. 72 to 96 hours after the administration of PMTP, the animals were killed by decapitation, their brain was rapidly removed, cooled in an ice-cold physiological saline solution, the striatum was excised and refrigerated in dry ice.

The tissues (in refrigerated condition) were weighed and homogenized in 1 ml of 0.4N perchloric acid solution containing 0.5% of $Na_2S_2O_5$, 0.25% of $Na_2EDTA$ and 100 ng of M-methyldopamine (internal standard for the determination of catecholamines) in an Ultra-Turrax equipment. The homogenate was centrifuged at 4° C. at 20,000 g for 10 minutes, then 0.8 ml of the supernatant was taken out. After adding 20 mg of activated aluminium oxide, the pH value of the solution was adjusted to 8 by adding 0.5M Tris solution and the tubes were shaken for 20 minutes. The aluminium oxide was settled, the supernatant was removed by suction and washed 3 times with 5 ml of distilled water each. The catecholamines adsorbed on the aluminium oxide were eluted with 1 ml of 0.05N perchloric acid. From a part of the eluate, dopamine was determined by using high pressure, liquid chromatography by means of electrochemical detection (Labor MIM Oe-320 pump, 4×150 mm Nucleosil 5 C-18 analytical column and a 4×20 mm Nucleosil 5 C-18 supplementary column; electrochemical detector fitted with a glassy-carbon working electrode and an $Ag/AgCl_2$ reference electrode; Eltron potentiostat, LKB 2110 2-channel recorder; with an oxidation potential of 600 mV and as mobile phase 0.1M $NaH_2PO_4$, 1 mM $Na_2EDTA$, 1 mM octanesulfonic acid containing 8.5% of acetonitrile; flow rate 1 ml/minute).

A decrease by 50 to 60% in the striatum dopamine level can be achieved by using the above method. The protection against the dopamine decrease induced by MPTP was calculated as follows:

$$\% \text{ inhibition} = \frac{\text{(treated with the compound + MPTP)} - \text{(treated with MPTP)}}{\text{(control)} - \text{(treated with MPTP)}} \times 100$$

As a reference drug, trihexyphenidyl hydrochloide (α-cyclohexyl-α-phenyl-1-piperidine-propanol hydrochloride) was used in a dose of 10 mg/kg (<0.1 mmole/kg). The animals perished on administration of a higher dose. The results are summarized in Table 2.

TABLE 2

| Compound | Dose mmole/kg | Route of administration | Inhibition of the dopamine decrease induced by MPTP % | n |
| --- | --- | --- | --- | --- |
| A | 0.1 | i.p. | 94 | 7 |
|   |     | p.o. | 87 | 7 |
| E | 0.1 | p.o. | 69 | 7 |
| Trihexyphenidyl.HCl | — | i.p. | 7 | 7 |

It is obvious from the data of Table 2 that, when administered orally and/or intraperitoneally to the animals before the treatment with MPTP, the compounds of the general formula (I) are capable to inhibit in a high degree or completely the neurotoxic dopamine-depleting action of MPTP. In addition, the compounds of the general formula (I) possess an advantageously low toxicity. Thus, the novel compounds of the invention represent a valuable therapeutical tool for influencing clinical cases, wherein a dopaminergic hypofunction exists as a consequence of the degeneration of the dopaminergic system or for other reasons.

According to the invention, the compounds of the general formula (I) are prepared by (a) reacting a compound of the general formula (II),

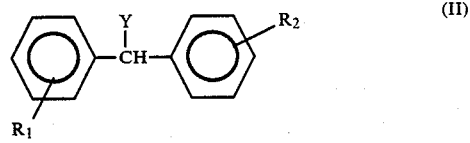

(II)

wherein $R_1$ and $R_2$ are as defined above and Y stands for halogen or a hydroxyl group or an OM group, wherein M means an alkali metal, with a piperazine derivative of the general formula (III),

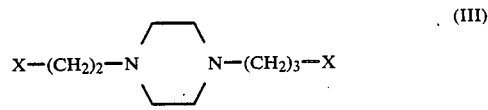

(III)

wherein X stands for a halogen atom or for an alkylsulfonyloxy, arylsulfonyloxy or hydroxyl group or an OM group, wherein M is as defined above, with the provisos that:

(1) X stands for a hydroxyl group or an OM group, wherein M is as defined above, when Y represents a halogen; or (2) X stands for a halogen atom or for an alkylsulfonyloxy or arylsulfonyloxy group when Y means a hydroxyl group or an OM group, wherein M is as defined above; or (b) reacting a compound of the general formula (IV),

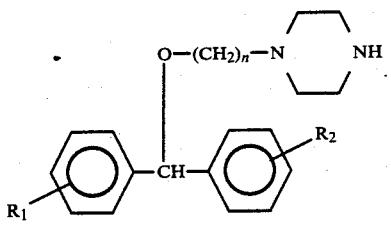

(IV)

wherein R₁ and R₂ are as defined above and both m and n have the value of 2 or 3, provided that n and m are different, with a compound of the general formula (V),

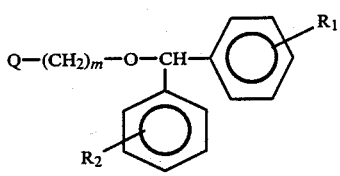

(V)

wherein R₁ and R₂ are as defined above and Q represents a halogen or an alkylsulfonyloxy or arylsulfonyloxy group; or (c) reacting a compound of the general formula (II), wherein R₁, R₂ and Y are as defined above, with a compound of the general formula (VI),

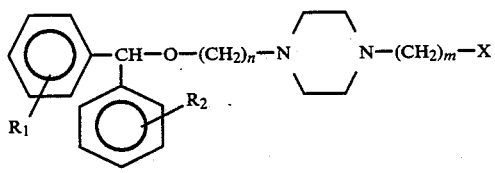

(VI)

wherein R₁, R₂, m, n and X are as defined above, with the provisos that:
(1) X stands for y hydroxyl group or an OM group, wherein M is as defined above when Y stands for a halogen; or
(2) X stands for a halogen or an alkylsulfonyloxy or arylsulfonyloxy group when Y means a hydroxyl group or an OM group, wherein M is as defined above, and, if desired, transforming a thus-obtained product prepared by using any one of processes (a) to (c) to an acid addition salt with an organic or inorganic acid or, if desired, transforming a product obtained in the form of an acid addition salt to the corresponding free base and/or, if desired, transforming a free base to its acid addition salt.

According to a preferred embodiment of process (a) of the invention, when either Y or X stands for an OM group, wherein M preferably means lithium, potassium or sodium, and the other one represents a halogen atom, preferably chlorine or bromine, then the reaction is carried out in an anhydrous inert organic solvent, suitably under an inert gas, e.g. in a nitrogen or argon atmosphere. Suitable solvents are e.g. aliphatic or aromatic hydrocarbons such as hexane, ligroin, benzene, toluene or xylene; aliphatic or alicyclic ethers such as dipropyl ether, dibutyl ether, tetrahydrofuran or dioxane; further dimethylsulfoxide, hexamethylphosphoramide or the mixtures of the above solvents. For preparing an alkoxide of a compound of the general formula (II) or (III) by means of an alkali metal tertiary-alkoxide, the appropriate tertiary alkanol or a mixture of this alkanol with the above solvents may be used.

When any one of Y and X stands for a hydroxyl group whereas the other one represents a halogen atom, preferably chlorine or bromine, or an alkylsulfonyloxy or arylsulfonyloxy group, preferably a methanesulfonyloxy or p-toluenesulfonyloxy group, then the reaction is accomplished in an inorganic or tertiary organic base which is suitable to bind the acid liberated in the reaction. Useful inorganic bases are e.g. alkali metal or alkali-earth metal carbonates such as potassium carbonate, sodium carbonate and the like; suitable tertiary organic bases are e.g. pyridine, triethylamine or tripropylamine.

The above-described conditions can conceivably be used in process (c), too.

According to process (b) of the invention, the reaction of a monosubstituted piperazine of the general formula (IV) with a compound of the general formula (V), wherein R₁, R₂, m, n and Q are as defined above, is carried out in an inert organic solvent, e.g. in an aromatic hydrocarbon such as benzene, toluene or xylene; or in an ether such as dibutyl ether or dioxane; or in a ketone such as 4-methyl-2-pentanone; or in an acid amide such as dimethylformamide; or in an ester type solvent such as ethyl acetate; or in a lower alkanol such as propanol or butanol; or in a halogenated hydrocarbon such as chlorobenzene. For binding the acid liberated in the reaction, organic or inorganic bases are useful, e.g. triethylamine, tripropylamine, 4-dimethylaminopyridine; or potassium carbonate, sodium carbonate and the like. For the promotion of this reaction, a small amount of a suitable metal iodide, e.g. sodium or potassium iodide, may be added as catalyst. For the acceleration of the reaction, an elevated temperature can be used: thus, it is suitable to accomplish this reaction at a temperature between 40° C. and the boiling point of the reaction mixture.

The product obtained by using any one of the processes of the invention is separated from the reaction mixture, e.g. in such a way that the reaction mixture is treated with water, the product is extracted into an organic solvent and, if necessary, it is further purified by known methods, e.g. distillation, chromatography or recrystallization.

If desired, the compounds of the general formula (I) can be transformed to their acid addition salts in a known manner. For the preparation of acid addition salts, inorganic or organic acids, e.g. hydrogen halides such as hydrogen chloride, hydrogen bromide and the like; sulfuric acid and phosphoric acid; formic, acetic, propionic, oxalic, glycollic, maleic, fumaric, succinic, tartaric, ascorbic, citric, malic, salicylic, lactic, benzoic, cinnamic, aspartic, glutamic, N-acetylaspartic or N-acetylglutamic acid; as well as alkanesulfonic acids such as methanesulfonic acid and arenesulfonic acids such as p-toluenesulfonic acid and the like can be used.

The acid addition salts can be prepared e.g. in such a way that the appropriate acids is added to a solution containing the compound of the general formula (I) in an inert solvent, e.g. to the ethanolic solution thereof, then the thus-obtained salt is precipitated by adding preferably a water-immiscible organic solvent such as ethyl ether.

The starting materials are known compounds or can be prepared by using processes known from the literature.

The benzhydrols of the general formula (II) may be synthetized e.g. by reacting the appropriate carbonyl compounds with Grignard reagents [see e.g.: M. S. Kharasch et al.: Grignard Reactions of Nonmetallic Substances, Ed. Prentice-Hall, Inc., pp. 138–143 (1954)] or by reducing the appropriate benzophenones with an alkali metal borohydride [E. Schenker: Angew. Chem. 73, 81 (1961)].

The preparation of the alcohols of the general formula (III) is described e.g. in CA 53, 22027d or in the British patent specification No. 807,750. The alcohols of the general formula (VI) can be prepared e.g. by reacting the alkoxides of the general formula (II) with 1-(2-hydroxyethyl)-4-(3-chloropropyl)piperazine or 1-(3-hydroxypropyl)-4-(2-chloroethyl)piperazine under conditions defined above for process (a). The latter piperazine derivatives can be synthetized e.g. by using the method of L. Toldy [Acta Chim. Acad. Sci. Hung. 42, 351 (1964)].

The alcohols of the general formulae (II), (III) and (VI) can be transformed to the appropriate alkoxides e.g. by using the methods described in Houben-Weyl: Methoden der Organischen Chemie VI/2, pp. 6–34 (1963).

The compounds of the general formulae (II), (III), (V) and (VI) can be prepared e.g. from the appropriate alcohols by using known methods. The halides may be obtained e.g. by treating the appropriate alcohols with suitable halogenating agents such as thionyl chloride, thionyl bromide, phosphorus pentachloride, phosphorus pentabromide or phosphorus oxychloride. The esters containing an alkylsulfonyloxy or arylsulfonyloxy group, e.g. the methanesulfonate or p-toluenesulfonate esters, can be obtained by reacting the alcohols with methanesulfonyl chloride or p-toluenesulfonyl chloride, respectively. The compounds of the general formula (V) may also be prepared by using e.g. the method of Sugasawa et al. [Org.. Synth. 33, 11 (1953)].

The monosubstituted piperazine derivatives of the general formula (IV) may be prepared, among other methods, e.g. by reacting the compounds of the general formula (V) with an excess of piperazine [Ind. Chim. Belge 22, 416 (1957)] though the process described by Kiichi Fujii et al. [J. Pharm. Soc. Japan 74, 1049 (1954)] may also be used.

The compounds of the invention can be transformed to pharmaceutical compositions. These compositions can be administered through an oral, rectal and/or parenteral route. For oral administration, the composition can be prepared in the form of tablets, dragées or capsules. For the preparation of oral compositions, e.g. lactose or starch can be used as vehicle. Suitable binding or granulating agents are e.g. gelatine, sodium carboxymethylcellulose, methylcelulose, polyvinylpyrrolidone or starch gum. As disintegrating agents, particularly potato starch or microcrystalline cellulose can be added, but ultraamylopectin or formaldehyde-casein is also useful. Talc, colloidal silicic acid, stearin as well as calcium and magnesium stearate or the like can be used as anti-adhesive and sliding agents.

Tablets can be prepared e.g. by wet granulation and subsequent compression. The mixture containing the active ingredients and vehicles and optionally a part of the disintegrating agent is granulated together with an aqueous, ethanolic or aqueous-ethanolic solution of the binding agents in an appropriate equipment, then the granulate is dried. Thereafter, the other disintegrating, sliding and anti-adhesive additives are mixed to the dried granulate and the mixture is compressed to tablets. Optionally the tablet is provided with a dissecting groove. The tablets can also be prepared by the direct compression of the mixture containing the active ingredient together with the needed additives. If desired, the tablets may be transformed to dragées by using the protective, flavouring and dyeing agents such as sugar, cellulose derivatives (methyl- or ethylcellulose or sodium carboxymethylcellulose), polyvinylpyrrolidone, calcium phosphate, calcium carbonate, food dyes, aromatizing agents, iron oxide pigments and the like which are commonly used in the pharmaceutical industry. For the preparation of capsules, the mixture of the active ingredients with the additives is filled into a capsule.

For rectal administration, the composition is prepared in the form of a suppository. In addition to the active ingredient, the suppository also contains a vehicle base material, the so-called "adeps pro suppositorio" (fat for suppository). As vehicles, vegetable fats such as hardened vegetable oils and the triglycerides of $C_{12-18}$ fatty acids, preferably vehicles with the trade mark Witepsol ® can be used. The active ingredient is homogeneously dispersed in the molten vehicle mass and then the suppositories are prepared by moulding.

For parenteral administration, the composition is prepared in the form of an injectable solution. For the preparation of injectable solutions, the active ingredients are dissolved in distilled water and/or various organic solvents, e.g. glycol ethers, optionally in the presence of solubilizing agents such as polyoxyethylene sorbitan monolaurate, monooleate or monostearate (Tween 20, Tween 60 and Tween 80, respectively). In addition, the injectable solution also contains various additives such as preservatives, e.g. benzyl alcohol, methyl or propyl 4-hydroxybenzoate, benzalkonium chloride, phenylmercury borate and the like; as well as antioxidants, e.g. ascorbic acid, tocopherol, sodium pyrosulfate and optionally complex forming agents such as an ethylenediamine tetraacetate salt for binding the metal traces, as well as buffers for adjusting the pH value and optionally a local anaesthetizing agent, e.g. lidocaine. The injectable solution containing the active ingredient of the invention is filtered before filling into the ampoule and sterilized after filling.

The daily doses depend upon the condition of the patient and the disease to be treated and are in general between 5 and 200 mg for adults in the case of oral administration.

The invention also relates to a method for treating diseases arising from a decrease in the dopamine level, i.e. from a hypofunction of the dopaminergic system. This process comprises the use of a therapeutically effective amount of an active ingredient of the general formula (I) or a pharmaceutically acceptable acid addition salt thereof to a subject in need of such treatment.

The invention is illustrated in detail by the aid of the following non-limiting Examples.

EXAMPLE 1

Preparation of 1-[2-bis(4-fluorophenyl)methoxy]ethyl]-4-[3-[bis(4-fluorophenyl)methoxy]propyl]piperazine dimaleate A suspension containing 2.5 g of 60% oily sodium hydride dispersion and 13.7 g of 4,4'-difluorobenzhydrol in 64 ml of anhydrous toluene is refluxed under nitrogen gas for 30 minutes while stirring, then a solution of 6.8 g of 1-(2-chloroethyl)-4-(3-chloropropyl)piperazine in 14 ml of anhydrous toluene is dropwise added. Refluxing is continued for additional 2 hours, then the mixture is cooled and water is added. The organic phase is separated, washed with water, dried over anhydrous potassium carbonate and evaporated under reduced pressure. The solution of the residue in benzene is filtered through an aluminium oxide layer and after evaporation an ethanolic maleic acid solution is added to the residue. The thus-obtained crystalline dimaleate melts at 189°–190° C.

The base is liberated from the above dimaleate by adding dilute aqueous ammonium hydroxide solution.

Analysis: Calculated for $C_{35}H_{36}F_4N_2O_2$ (base) C 70.93; H 6.12; F 12.82; N 4.73%; found C 71.01; H 6.03; F 12.70; N 4.86%.

The following compound is prepared analogously to the process described in Example 1:
1-[2-[(4-Methoxyphenyl)-(3-trifluoromethylphenyl)methoxy]ethyl]-4-[3-[(4-methoxyphenyl)-(3-trifluoromethylphenyl)methoxy]propyl]piperazine dimaleate, m.p.: 166°–167° C., is prepared by reacting 1-(2-hydroxyethyl)-4-(3-hydroxypropyl)piperazine dimethanesulfonate with the sodium salt of 3-(trifluoromethylphenyl)-4'-methoxybenzhydrol.

Analysis: Calculated for $C_{39}H_{42}F_6N_2O_4$ (base) C 65.35; H 5.91; F 15.90; N 8.93%; found C 65.50; H 6.00; F 15.98; N 8.72%.

EXAMPLE 2

Preparation of 1-[3-[(4-Fluorophenyl)-phenylmethoxy]-propyl]-4-[2-(diphenylmethoxy)ethyl]piperazine 10.1 g of benzhydrol are refluxed with 6.2 g of potassium tertiary butoxide in 100 ml of anhydrous tertiary butanol under argon gas for 30 minutes, then 19.6 g of 1-[3-[(4-fluorophenyl)-phenylmethoxy]propyl]-4-(2-chloroethyl)piperazine dissolved in 40 ml of anhydrous tertiary butanol are dropwise added. The mixture is boiled for one additional hour, then evaporated to about 40 ml under reduced pressure and after adding water it is extracted with benzene. The organic phase is dried over anhydrous magnesium sulfate and, after evaporating benzene under reduced pressure, the residue is fractionally distilled. The aimed compound boils at 247°–250° C./0.01 Hgmm.

Analysis: Calculated for $C_{35}H_{39}FN_2O_2$ C 78.03; H 7.30; F 3.53; N 5.20%; found C 79.21; H 7.11; F 3.69; N 5.37%.

EXAMPLE 3

Preparation of 1-[2-[(2-methylphenyl)-(4-fluorophenyl)methoxy]ethyl]-4-[3-[(2-methylphenyl)-(4-fluorophenyl)methoxy]propyl]piperazine dimaleate A solution containing 9.4 g of 1-(2-hydroxyethyl)-4-(3-hydroxypropyl)piperazine, 29.3 g of 2-methyl-4'-fluorobenzhydryl chloride and 24 ml of tripropylamine in 120 ml of dimethylformamide is refluxed for 8 hours while stirring, then evaporated under reduced pressure. After adding water to the residue and extracting with benzene, the organic phase is washed with water, dried over anhydrous sodium sulfate and the solvent is evaporated under reduced pressure. The residue is dissolved in methanol, clarified with charcoal, filtered and an ethereal maleic acid solution is added to the filtrate. The precipitate is filtered and recrystallized from methanol to give the aimed dimaleate, m.p.: 178°–179.5° C.

Analysis: Calculated for $C_{37}H_{42}F_2N_2O_2$ (base) C 75.99; H 7.24; F 6.50; N, 4.79%; found C 76.20; H 7.33; F 6.63; N 4.88%.

EXAMPLE 4

Preparation of 1-[3-[(4-fluorophenyl)-phenylmethoxy]propyl]-4-[2-[(4-fluorophenyl)-phenylmethoxy]ethyl]piperazine dimaleate A mixture containing 6.6 g of 1-[3-[(4-fluorophenyl)-phenylmethoxy]propyl]piperazine, 6.6 g of 2-[(4-fluorophenyl)-phenylmethoxy]ethyl chloride, 4.1 g of anhydrous powdered potassium carbonate and 0.5 g of potassium iodide in 70 ml of methyl isobutyl ketone is refluxed under stirring for 17 hours, then cooled down and evaporated under reduced pressure. After adding water and chloroform to the residue, the organic phase is separated, dried over anhydrous magnesium sulfate and evaporated under reduced pressure. The residue is dissolved in anhydrous ether and an ethereal solution of maleic acid is added. The precipitate is recrystallized from methanol to give the aimed dimaleate, m.p.: 176°–177° C.

Analysis: Calculated for $C_{35}H_{38}F_2N_2O_2$ (base) C 75.51; H 6.88; F 6.83; N 5.03%; found C 75.55; H 7.11; F 6.65; N 5.28%.

The following compound is prepared analogously to the process described in Example 4:
1-[2-(Diphenylmethoxy)ethyl]-4-[3-(diphenylmethoxy)propyl]piperazine dimaleate, m.p.: 175°–176° C., is prepared by reacting 3-(diphenylmethoxy)propyl p-toluenesulfonate with 1-[2-diphenylmethoxy)ethyl]piperazine.

Analysis: Calculated for $C_{35}H_{40}N_2O_2$ (base) C 80.73; H 7.74; N 5.38%; found C 80.88; H 7.66; N 5.50%.

EXAMPLE 5

Preparation of 1-[2-[bis(4-chlorophenyl)methoxy]ethyl]-4-[3-[bis(4-chlorophenyl)methoxy]propyl]piperazine dimaleate A solution of 5.7 g of 1-(2-hydroxyethyl)-4-(3-hydroxypropyl)piperazine, 14.3 ml of tripropylamine and 20.4 g of 4,4'-dichlorobenzhydryl chloride in 100 ml of anhydrous xylene is refluxed under stirring for 15 hours, then cooled and water is added. The organic phase is separated, washed with water, dried over anhydrous magnesium sulfate and evaporated under reduced pressure. The residue is purified on a Kieselgel column by using chloroform as eluant. The appropriate fractions are evaporated under reduced pressure, the residue is dissolved in ethanol and treated with an ethanolic maleic acid solution. The crystalline dimaleate is filtered and dried, m.p.: 192°–194° C.

Analysis: Calculated for $C_{35}H_{36}Cl_4N_2O_2$ (base) C 63.84; H 5.51; Cl 21.54; N 4.25%; found C 63.62; H 5.67; Cl 21.70; N 4.28%.

EXAMPLE 6

Preparation of 1-[2-[(4-trifluoromethylphenyl)-(4-fluorophenyl)-methoxy]ethyl]-4-[3[(4-trifluoromethylphenyl)-(4-fluorophenyl)-methoxy]propyl]piperazine dimaleate A suspension containing 5.7 g of 1-(2-hydroxyethyl)-4-(3-hydroxypropyl)piperazine, 2.7 g of 60% oily sodium hydride dispersion and 50 ml of anhydrous xylene is refluxed under argon gas while stirring until the evolution of hydrogen ceases. Then 22.3 g of 4-fluoro-4'-(trifluoromethyl)benzhydryl bromide dissolved in 50 ml of anhydrous xylene are dropwise added and the mixture is boiled for additional 3 hours. After cooling, the reaction mixture is poured into water, the organic phase is separated, washed with water, dried over anhydrous sodium sulfate and evaporated under reduced pressure. The residue is dissolved in ethanol, clarified with charcoal and an ethanolic maleic acid solution is added. The precipitate is filtered and recrystallized from methanol to give the aimed dimaleate, m.p.: 181°-183° C.

Analysis: Calculated for $C_{37}H_{36}F_8N_2O_2$ (base) C 64.15; H 5.24; F 21.94; N 4.04%; found C 64.33; H 5.46; F 22.85; N 4.20%.

EXAMPLE 7

The compounds of the invention can be formulated e.g. to the pharmaceutical compositions described hereinafter.

Preparation of tablets 50 g of active ingredient, 92 g of lactose, 40 g of potato starch, 4 g of polyvinylpyrrolidone, 6 g of talc, 1 g of magnesium stearate, 1 g of colloidal silicon dioxide (Aerosil) and 6 g of ultraamylopectin are mixed, granulated as wet and compressed to tablets each of which weighes 200 mg and contains 50 mg of active ingredient which is 1-[2-[bis(4-chlorophenyl)methoxy]ethyl]-4-[3-[bis(4-chlorophenyl)methoxy]propyl]piperazine dimaleate.

Preparation of dragées

The tablets prepared as described above are covered with a coat consisting of sugar and talc, then the dragées are polished by using a mixture of bee wax and carnauba wax.

Each dragée weighes 250 mg.

Preparation of a suspension

The components of 100 ml of suspension are as follows:

| | |
|---|---|
| Active ingredient | 1.0 g |
| Sodium hydroxide | 0.26 g |
| Citric acid | 0.30 g |
| Nipagin (methyl 4-hydroxybenzoate) | 0.10 g |
| Carbopol 940 (polyacrylic acid) | 0.30 g |
| Ethanol (96%) | 1.00 g |
| Raspberry flavour | 0.60 g |
| Sorbitol (70% aqueous solution) | 71.00 g |
| Distilled water for injection purpose q.s. ad | 100 ml |

Carbopol is added in small portions to a solution containing nipagin and citric acid in 20 ml of distilled water under vigorous stirring, then the solution is left to stand for 10 to 12 hours. Thereafter, the above-given amount of sodium hydroxide dissolved in 1 ml of distilled water is added, sorbitol is mixed in, finally the ethanolic solution of the raspberry flavour is added while stirring. The active ingredient is added to the vehicle in small portions, then the mixture is transformed to a suspension by means of an immersed homogenizer. Finally, the suspension is filled up to 100 ml with distilled water and the thus-obtained suspension syrup is passed through a colloid mill. The active ingredient is 1-[2-[bis(4-fluorophenyl)methoxy]ethyl]-4-[3-[bis(4-fluorophenyl)methoxy]propyl]piperazine dimaleate.

We claim:
1. A 1,4-disubstituted piperazine of the formula (I),

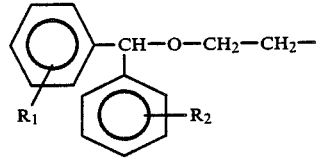
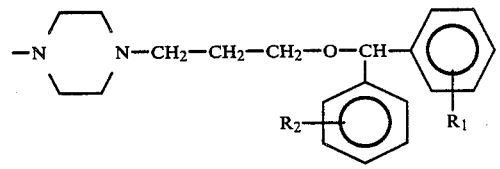

wherein
$R_1$ and $R_2$ are the same or different and stand for hydrogen or halogen or a lower alkyl, trihalomethyl or lower alkoxy group,
and pharmaceutically acceptable acid addition salts thereof.

2. A pharmaceutical composition for treating diseases arising from dopamine deficiency comprising, as active ingredient, an effective amount of the 1,4-disubstituted piperazine of claim 1, or a pharmaceutically acceptable acid addition salt thereof in admixture with carriers and/or additives commonly used in the pharmaceutical industry.

3. A 1,4-disubstituted piperazine selected from the group consisting of 1-[2-[bis(4-fluorophenyl)methoxy]ethyl]-4-[3-[bis(4-fluorophenyl)methoxy]propyl]piperazine, 1-[2-diphenylmethoxy)ethyl]-4-[3-(diphenylmethoxy)propyl]piperazine and pharmaceutically acceptable acid additional salts thereof.

4. A method of treating diseases arising from a decrease in the dopamine level, which comprises administering to a mammal (including man) in need of such treatment a therapeutically effective amount of a 1,4-disubstituted piperazine of the formula (I)

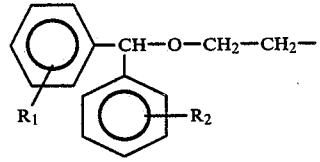
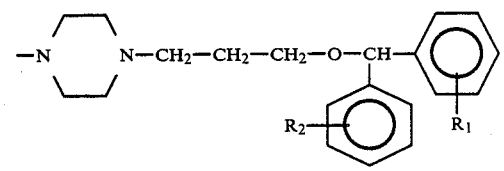

wherein
$R_1$ and $R_2$ are the same or different and stand for hydrogen or halogen or a lower alkyl, trihalomethyl or lower alkoxy group,
or pharmaceutically acceptable acid addition salts thereof.

5. The method of claim 4 wherein said 1,4-disubstituted piperazine is selected from the group consisting of 1-[2-[bis(4-fluorophenyl)methoxy]ethyl-4-[3-[bis(4-fluorophenyl)methoxy]propyl]piperazine, 1-[2-[(4-methoxyphenyl)-(3-trifluoromethylphenyl)methoxy]ethyl]-4-[3-(4-methoxyphenyl)-(3-trifluoromethylphenyl)methoxy]propyl]piperazine, 1-[2-[bis(4-chlorophenyl)methoxy]ethyl]-4-[3-[bis(4-chlorophenyl)methoxy]propyl]piperazine, 1-[2-[(2-methylphenyl)-(4-fluorophenyl)methoxy]ethyl]-4-[3-[2-methylphenyl)-(4-fluorophenyl)methoxy]propyl]piperazine, and 1-[2-(diphenylmethoxy)ethyl]-4-[3-(diphenylmehoxy)propyl]piperazine.

* * * * *